United States Patent [19]

Tanguy

[11] Patent Number: 4,943,291
[45] Date of Patent: Jul. 24, 1990

[54] DRILLING FEELER, IN PARTICULAR FOR POSITIONING AND SECURING A MEDULLARY NAIL

[75] Inventor: Christian Tanguy, Choisy le Roi, France

[73] Assignee: Zimmer S.A., Vitry sur Seine Cedex, France

[21] Appl. No.: 286,681

[22] Filed: Dec. 19, 1988

[30] Foreign Application Priority Data

Dec. 18, 1987 [FR] France .................. 87 17716

[51] Int. Cl.⁵ .................................................. A61F 5/04
[52] U.S. Cl. ............................................. 606/64; 606/80
[58] Field of Search .................. 606/57, 59, 60, 62, 606/63, 64, 67, 80, 96, 98, 139

[56] References Cited

U.S. PATENT DOCUMENTS

| | | | |
|---|---|---|---|
| 2,316,297 | 4/1943 | Southerland et al. | 606/139 |
| 4,016,874 | 4/1977 | Maffei et al. | 606/62 |
| 4,103,683 | 8/1978 | Neufeld | 606/67 |
| 4,586,497 | 5/1986 | Dapra et al. | 606/80 |
| 4,625,718 | 12/1986 | Olerud et al. | 606/98 |
| 4,781,181 | 11/1988 | Tanguy | 606/80 |

*Primary Examiner*—Robert A. Hafer
*Assistant Examiner*—Charles H. Sam
*Attorney, Agent, or Firm*—Marvin E. Jacobs

[57] ABSTRACT

The feeler is placed in alignment with the axis of a pin or screw inlet hole of the wall of the nail and is mounted at the distal end of a driving rotating spindle, at least partially flexible, the distal end of the spindle bearing the tool being housed in a bore of a protruding sleeve carried by a sliding block between a disengagement position allowing the sliding of the head in the nail and an engagement position, with application to feelers intended to bore, in bone surgery, a transversal hole from a medullary channel.

5 Claims, 2 Drawing Sheets

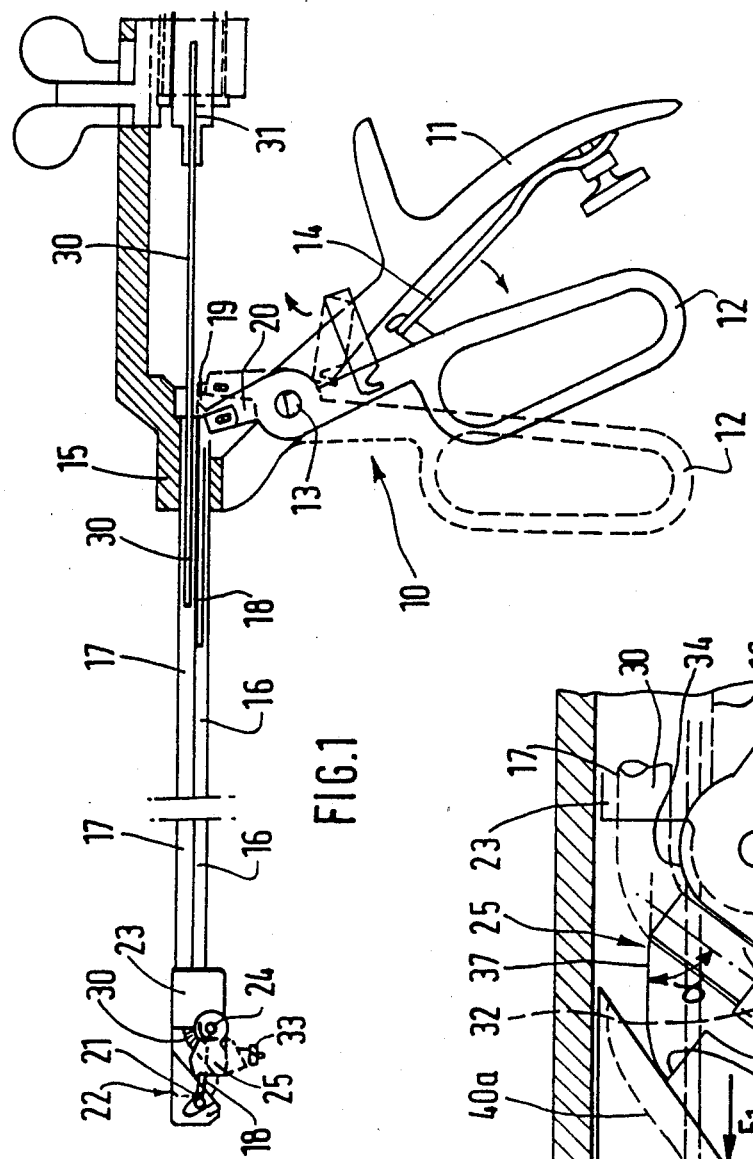
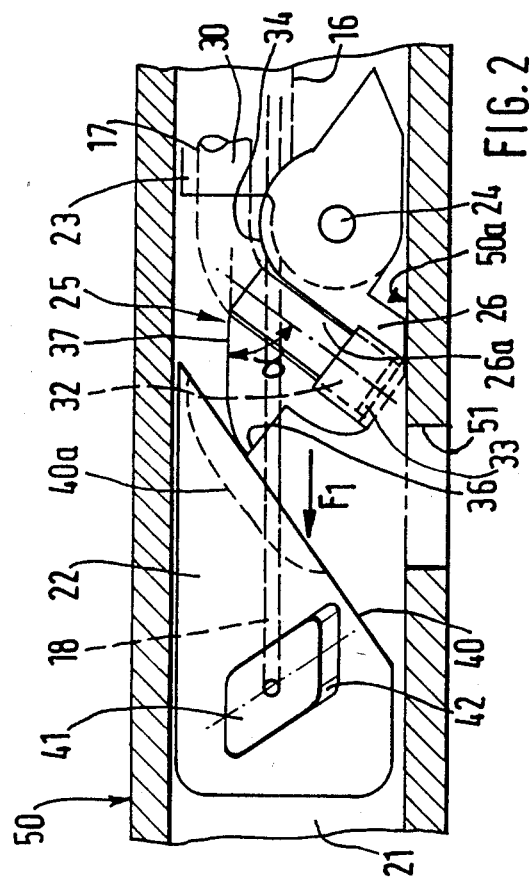

DRILLING FEELER, IN PARTICULAR FOR POSITIONING AND SECURING A MEDULLARY NAIL

BACKGROUND OF THE INVENTION

1. Field of the invention

The present invention concerns a drilling feeler, intended in particular for positioning a medullary nail, i.e. in bone surgery for axially securing a nail having an annular cross-section by means of pins simultaneously passing through the bone and the nail in a transversal direction.

2. Summary of the prior art

Are already known, especially from earlier French patent applications filed in the name of the applicant, 85.12777 dated August 25, 1985 and 86.11270 dated Aug. 13, 1986, feelers of this type in which a drilling head, mounted on the end of a spindle at least partially flexible and driven in rotation through the intermediary of coupling means, by a rotary motor, is guided within a guiding and positioning head introduced into the medullary nail. This guiding head is displaced in the said nail until the drilling head is placed opposite an inlet hole provided in the annular wall of this nail. Means are provided for blocking in rotation and in axial position the guiding head in this nail, so that the drilling head is correctly positioned during drilling and maintains its position.

However, in the feelers proposed up to now, these blocking means are produced, on the one hand, for the rotation, by the form of the cross-section of the guiding head, complementary with the cross-section of the nail, on the other hand, for the axial position, by ratcheting of a ball carried by this head, and engaged in an appropriately disposed bore on the wall of the nail, do not ensure a completely satisfactory locking of the axis of the drilling head; this results in particular from the operating clearance required between the guiding head and the internal wall of the nail and also due to the fact that the ratcheting ball is placed at a distance from the drilling head. Furthermore, experience has shown that the boring drill tends to slide on the bone surface and that it is necessary, to avoid any deviation of the drilling hole, to guide correctly the boring drill and to make it attack the surface of the bone along a line perpendicular to the surface.

The present invention aims at producing a drilling feeler that does not present these drawbacks.

The feeler according to the invention, intended to be associated to a medullary nail in which, through external gripping means, is introduced into the medullary nail and is placed in alignment with the axis of an inlet pin or screw hole of the wall of this nail, a drilling tool integral with a sliding block bearing means for positioning and blocking the said nail, this tool being mounted at the distal end of a driving rotating spindle, at least partially flexible, wherein the distal end of the spindle carrying the tool is housed in a bore of a sleeve protruding from a drilling head, said head being movable around an axle carried by the block sliding between a disengagement position allowing the sliding of the said head in the nail and an engagement position in which the sleeve is engaged in the inlet pin or screw hole, the feeler furthermore comprising a blocking wedge hinged to the end of a rod connected to the gripping means, this wedge being adapted to move closer to or away from the drilling head, in order to respectively maintain it in engagement position or allow its tilting towards disengagement position.

According to another characteristic, the drilling head comprises a nose-piece turned towards the blocking wedge, this nose-piece provided with a flattened portion, perpendicular to the axis of the sleeve and adapted to enter into contact with the internal wall of the nail in engagement position of the drilling head and a slope bearing surface adapted to cooperate, for this same engagement position, with a slope face of the wedge which is recalled towards the said drilling head through the intermediary of the rod cooperating with the gripping means.

According to another embodiment, the rod hingedly connected to the wedge and the driving spindle of the drilling head are housed in two parallel tubes, at the distal end of which is fixed the sliding block, the other end of these tubes being fixed to a body integral with the gripping means, these consisting of a clip comprising a fixed part integral with the said body and a movable part about a common axis and an extension of which is hinged to the proximal end of the rod, a spring urging the movable parts to spread apart from each other and thus to move closer together the wedges of the block. The distal end of the rod is connected to the blocking wedge through the intermediary of a slide movable in a slope ramp, provided in the wedge and having an axis substantially normal to the slope face, in such a manner that a return of the wedge towards the drilling head, in contact with the slope bearing surface of this head, pushes this wedge into contact with the internal wall of the nail by consolidating the locking of the assembly.

According to one advantageous disposition of the feeler, the sliding block and the wedge present at least partially complementary cross-sections of the cross-section of the associated medullary nail.

BRIEF DESCRIPTION OF THE DRAWINGS

Other features, objects and advantages of the invention will become apparent from the following description, given solely by way of non-limitative illustration, with reference to the appended drawings in which:

FIG. 1 is a schematic view of the side of the feeler according to the invention, intended to be associated to a medullary nail (not represented);

FIG. 2 is a cross-sectional view in detail with torn-away parts of the distal end of the feeler of FIG. 1, in approach position of one of the pin or screw inlet holes provided in the wall of the associated medullary nail;

DETAILED DESCRIPTION OF A PREFERRED EMBODIMENT

Figure 3:
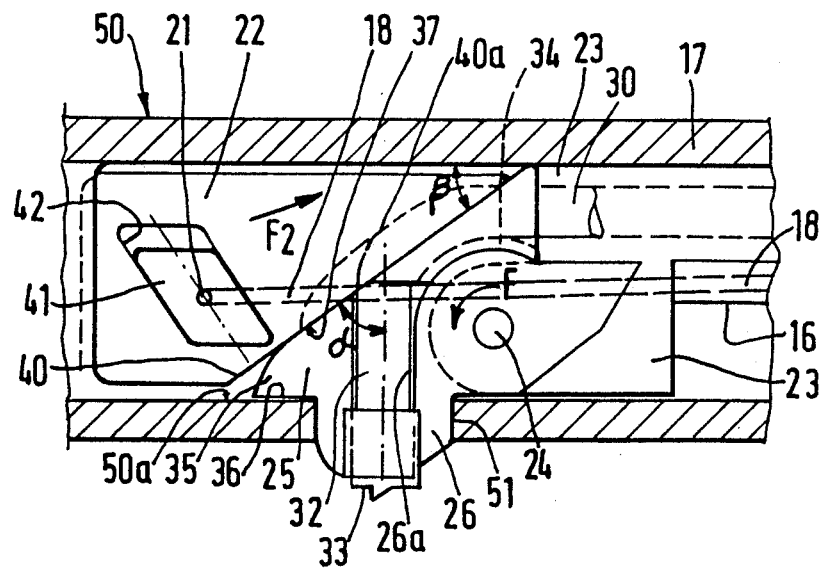
FIG. 3 is a view similar to that of FIG. 2, of the feeler according to the invention occupying an engagement position of the drilling head in the pin or screw inlet hole already bored in the wall of the medullary screw.

The feeler according to the invention comprises, at its proximal end, a control handle 10, forming a clip, with a fixed part 11 and a movable part 12, hinged to the handle about a transversal axis 13, a spring 14 urging the two parts to move away from each other.

A cylindrical body 15 is attached to the fixed part 11 and is extended towards the distal part of the feeler by a set of two parallel tubes 16 and 17. A sliding rod 18 is disposed in the tube 16, one of the ends 19, of this rod being hinged to an arm 20 of the movable part 12 of the handle and the other end, 21, of this rod carrying a wedge 22 for guiding and blocking the feeler, the description of which will be given herein-after.

The two tubes 16 and 17 are joined to each other according to their length and carry at their common distal ends a block 23 upon which is hinged, about an axis 24 perpendicular to the axis of the tubes, a drilling head 25. This drilling head which comprises a protruding sleeve 26, internally bored and perpendicular to the axle 24, is movable between a disengagement position (FIG. 2) in which the head is tilted so that the axis of the sleeve 26 creates an obtuse angle with the tubes 16, 17 and an engagement position (FIG. 3) in which the drilling head is tilted in the direction of the arrow F, the axis of the said head thus being substantially perpendicular to the tubes 16 and 17.

A drill driving spindle 30, at least partially flexible, is engaged in the tube 17 and is coupled at its proximal end 31 to driving rotating means (not represented) and carries at its distal end 32, engaged in the bore forming the guiding body 26a of the sleeve 26, a drilling tool 33 such as a drilling head. An appropriate groove 34 is provided in the head 25 for the passage, without sharp elbow of the cable 30.

The drilling head 35 carries a terminal nose-piece 35 which forms a flattened portion 36, perpendicular to the axis of the sleeve 26 (and parallel to the axis 24) and a slope surface bearing 37, which is also parallel to the axis 24 and forming an $\alpha$ angle, close to 45° for example with the axis of the sleeve 26.

The nose-piece 35, and more particularly the slope bearing surface 37, are adapted to cooperate with a slope face 40 of the wedge 22; this face 40 creates an angle $\beta$, complementary with the angle $\alpha$, with the axis of the tubes 16, 17 and is provided with a hollow groove 40a for guiding the flexible spindle 30 of the drilling tool 33.

The wedge 22 which has a cross-section slightly smaller than that of the associated medullar nail is integral with the end 21 of the rod 18 through the intermediary of a slide 41 fixed thereto and movable in a ramp 42, having an axis substantially normal to the face 40.

In the approach position of the feeler, the two parts 11 and 12 of the handle being moved closer together, against the spring 14, the rod 18 moves apart, according to the arrow $F_1$, the wedge 40 of the head 25. This head can be shifted in disengagement position (FIG. 2) and introduced, with the wedge 22, into the medullary nail 50, the sleeve 26 being slightly in withdrawal position with respect to the lower edge of the wedge 22.

The parts of the handle still being maintained close together, the assembly is thus displaced towards one of the inlet pin or screw holes 51, previously drilled and bored with precision in the medullary nail, prior to the placing in position thereof in the medullary channel of the bone.

When the sleeve 26 is straight above the hole 51, the control handle 10 is released. Under the action of the spring 14, the wedge 22 is returned towards the head 25 and causes it to shift about the arrow F. The sleeve 26 is engaged in the hole 51; the wedge 22, through the cooperation of the bearing surface 37 and of the face 40, comes into contact with the internal wall 50a of the medullary nail, opposite the hole 51, according to the arrow $F_2$ of FIG. 3 following guiding of the slide 41 in the ramp 42. This results in very effective blocking of the feeler in the medullary nail. The drilling of the passage hole in the bone of the screw or of the fixation pin of the medullary nail 50 can thus be performed, by putting in rotation and moving forward of the drilling tool 33, without any risk of axial displacement thereof since the maintaining in axial and radial position of the drilling tool 33 is ensured through the engagement of the sleeve 26 in the hole 51 previously drilled.

It should be noted that the blocking wedge 22, in addition to the shifting of the drilling head 25, allows compensation of a possible tightening of the cross-section of the nail, being able to intervene during placing in position of this latter. In fact, the cross-section of the nail being generally resilient, it is often led, during its passage in the smallest cross-section of the medullary channel (at mid-height of the bone) to be deformed in a plastic manner, thus, not completely reversible, so that a tool not having a variable geometry, such as here due to the movable wedge, could not, in certain cases, sink down to the bottom of the nail.

Once this drilling operation has been finished, it is sufficient to bring back the drilling tool into the sleeve 26, then to move together the parts 11, 12 of the control handle 10. The wedge 40, by sliding of the rod 20, is moved apart from the drilling head 25 and, during traction on the tubes 16, 17 in order to ensure the withdrawal of the assembly of the feeler, the drilling head shifts in the direction contrary to the arrow F and comes back into the disengagement position of FIG. 2.

Figure 4:
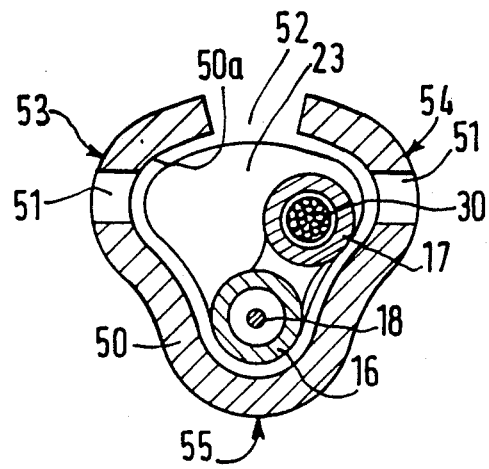
FIG. 4 is a view in transversal cross-section with respect to an inlet hole of the medullary nail associated to the drilling feeler, this nail being provided with a continuous longitudinal slot and a three-cusped section.

FIG. 4 is a view in transversal cross-section of the medullary nail 50, intended to be associated to the feeler according to the invention. This nail, obtained by folding of a relatively thick sheet made of biocompatible metal such as stainless steel or titanium, is provided with a continuous longitudinal slot 52, a cross-section having a generally three-cusped form (with two lateral lobes 53 and 54 in each of which are bored several holes 51 longitudinally aligned and a bottom lobe 55 not provided with a bore but assisting to the radial guiding of the feeler) and is provided with inlet screw or pin holes 51 previously drilled and bored with precision and aligned in pairs.

It receives the feeler and, in particular the block 23 fixed to the distal end of the tubes 16 and 17 and the cross-section of which is substantially similar to and slightly smaller than the internal section of the nail, i.e. complementary with the cross-section of the internal wall of the medullary nail, which guarantees a good radial positioning of the feeler which thus comes, simply by translation opposite one or other of the bores of the holes 51, on one side of the medullary nail.

It is well understood that the present invention is in no way limited to the embodiments described and represented herein-above and can be adapted to numerous variants available to those skilled in the art without departing from the scope and spirit of the invention.

I claim:

1. Drilling feeler, in particular for positioning and fixing a medullary nail in which, through external gripping means, is introduced into the medullary nail and is placed in alignment with the axis of an inlet pin or screw hole of the wall of this nail, a drilling tool integral with a sliding block bearing means for positioning and blocking the said nail, this tool being mounted at the distal end of a driving rotating spindle, at least partially flexible, wherein the distal end of the spindle carrying the tool is housed in a bore of a sleeve protruding from a drilling head, said head being movable around an axle carried by the block sliding between a disengagement position allowing the sliding of the said head in the nail and an engagement position in which the sleeve is engaged in the inlet pin or screw hole, the feeler furthermore comprising a blocking wedge hinged to the end of a rod connected to the gripping means, this wedge being adapted to move closer to or away from the drilling head, in order to respectively maintain it in engagement position or allow its tilting towards disengagement position.

2. Feeler according to claim 1, wherein the drilling head comprises a nose-piece turned towards the blocking wedge, this nose-piece provided with a flattened portion, perpendicular to the axis of the sleeve and adapted to enter into contact with the internal wall of the nail in engagement position of the drilling head and a slope bearing surface adapted to cooperate, for this same engagement position, with a slope face of the wedge which is recalled towards the said drilling head through the intermediary of the rod cooperating with the gripping means.

3. Feeler according to claim 1, wherein the rod hingedly connected to the wedge and the driving spindle of the drilling head are housed in two parallel tubes, at the distal end of which is fixed the sliding block, the other end of these tubes being fixed to a body integral with the gripping means, these consisting of a clip comprising a fixed part integral with the said body and a movable part about a common axis and of which an extension is hinged to the proximal end of the rod, a spring tending to spread apart the movable parts from each other and to move closer together thus the wedges of the block.

4. Feeler according to claim 1, wherein the distal end of the rod is connected to the blocking corner through the intermediary of a slide movable in a slope ramp, provided in the wedge and having an axis substantially normal to the slope face, in such a manner that a return of the wedge towards the drilling head, in contact with the slope bearing surface of this head, pushes this wedge into contact with the internal wall of the nail by consolidating the locking of the assembly.

5. Feeler according to claim 1, wherein the sliding block and the wedge present complementary cross-sections at least partially of the cross-section of the associated medullary nail.

* * * * *